United States Patent [19]
Lin

[11] Patent Number: 5,824,833
[45] Date of Patent: Oct. 20, 1998

[54] DIMERIZATION CATALYST AND PROCESS USING ALKYL ALUMINUM ALKOXIDE

[75] Inventor: Kaung-Far Lin, Baton Rouge, La.

[73] Assignee: Amoco Corporation, Chicago, Ill.

[21] Appl. No.: 345,964

[22] Filed: Nov. 28, 1994

[51] Int. Cl.$^6$ ...................................................... C07C 2/26
[52] U.S. Cl. ............................................ 585/511; 585/512
[58] Field of Search .................................... 585/510, 511, 585/512, 522

[56] References Cited

U.S. PATENT DOCUMENTS

| | | | |
|---|---|---|---|
| 2,959,607 | 11/1960 | Werber et al. | 260/448 |
| 2,962,513 | 11/1960 | Meiners et al. | 260/448 |
| 3,113,986 | 12/1963 | Breslow et al. | 260/683.9 |
| 3,424,815 | 1/1969 | Cannell | 260/683.15 |
| 3,784,623 | 1/1974 | Motz | 260/677 R |
| 4,973,788 | 11/1990 | Lin et al. | 585/511 |
| 5,536,859 | 7/1996 | Lin et al. | 556/190 |

*Primary Examiner*—Bekir L. Yildirim
*Attorney, Agent, or Firm*—James R. Hense; Stephen L. Hensley

[57] ABSTRACT

A process for producing an vinylidene olefin of the formula

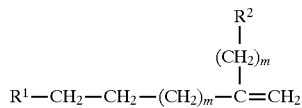

where $R^1$ and $R^2$ are the same or different and are hydrogen or alkyl and m is an integer of from 0 to 18, with a catalytically effective amount of a mixture of i) an aluminum compound of the formula $R^4{}_n Al(OR^5)_p$ where $R^4$ and $R^5$ are the same or different and are alkyl, n is an integer from 0.75 to 2.75, and p is an integer from 0.25 to 2.25, the sum of n and p being 3, at a temperature of from about 120° C. to about 200° C. whereby a major amount of said vinylidene and deep internal olefin dimer is produced and only a minor amount of a beta internal olefin isomer.

6 Claims, No Drawings

DIMERIZATION CATALYST AND PROCESS USING ALKYL ALUMINUM ALKOXIDE

FIELD OF THE INVENTION

This invention relates to a catalyst useful in the dimerization of alpha-olefins. More particularly, this invention relates to an alkyl aluminum alkoxide catalyst to achieve dimerization of alpha-olefins.

BACKGROUND OF THE INVENTION

Organoaluminum compounds have been previously utilized in the preparation of catalysts such as Ziegler-type catalysts. These catalysts preparations are based on the ability of organoaluminum compounds to act as reducing agents, i.e., reducing a transition metal to the zero valence state, e.g., U.S. Pat. No. 3,113,986.

U.S. Pat. No. 2,959,607 discloses the preparation of aluminum alkyls which contain at least one n-octyl group by subjecting octene-2 to the action of at least a stoichiometric amount of triisobutyl aluminum in the presence of a cobalt chloride catalyst at substantially atmospheric pressure. The catalyst apparently acts as both an isomerization and displacement catalyst in this process. The aluminum alkyls can be oxidized and hydrolyzed to make octanol-1.

U.S. Pat. No. 2,962,513 discloses a process for forming longer chain aluminum alkyls by a catalyzed olefin displacement of ethylene from ethyl aluminum compounds using a 100 to 300 percent stoichiometric excess of $C_3$ or higher alpha-olefins. The process uses salts and oxides of Group VIII metal as catalysts at temperatures of from about 50 to 200° C. at atmospheric pressure. Ethylene is evolved in the reaction.

U.S. Pat. No. 3,784,623 discloses the control of the increased tendency of the alpha-olefins to isomerize to internal olefins, which tendency is associated with catalytic displacement, by adding inhibitors or catalyst inactivators to the process.

U.S. Pat. No. 4,973,788 discloses a trialkylaluminum catalyst that is useful for dimerizing various vinyl-olefin monomers. The term "vinyl-olefin" is the same as "alpha-olefin" and used interchangeably. This patent notes that the organoaluminum catalyst is used in low concentrations, since high quantities promote the formation of undesirable monomers and dimeric internal olefins.

BRIEF SUMMARY

In accordance with this invention, there is provided a catalyst that is an alkyl aluminum alkoxide of the formula $R^4{}_nAl(OR^5)_p$, where $R^4$ and $R^5$ are alkyl and n is from 0.75 to 2.75, p is from 0.25 to 2.25 and the sum of n and p is 3.

The catalyst is useful in a process for preparing vinylidene olefins of the formula

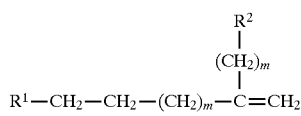

where $R^1$ and $R^2$ are the same or different and are hydrogen or alkyl and m is an integer from 0 to 18.

The vinylidene olefins are useful when oligomerized as oils. Depending on their viscosity, different applications for such oils are known, e.g., as lubricants. These materials are mixtures of different percentages of dimer, trimer, tetramer, pentamer and higher oligomers which oligomers are produced in different proportions in the oligomerization process. In order to increase the viscosity, processes are used which either produce more of the higher oligomers or some of the lower oligomers are removed such as by distillation. Most low viscosity dimer and trimer products are obtained as by-products of the production of higher viscosity synthetic oils. Due to the increasing use of dimers in applications such as low temperature lubricants and drilling fluids, methods for their preferential production are of interest.

DETAILED DESCRIPTION

In the specification: olefins are referred to as "vinyl olefins" or $R-CH=CH_2$; "vinylidene olefins" or

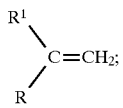

and internal olefins, which are sub-divided as: "di-substituted olefins" ($R^1-CH=CH-R$), "tri-substituted olefins"

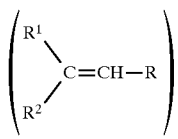

and "tetra-substituted olefins"

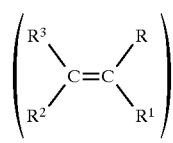

wherein R, $R^1$, $R^2$ and $R^3$ represent a hydrocarbyl group. Internal olefins are also classified as "beta-internal olefins" in which the double bond is connected to the beta-carbon atom as in:

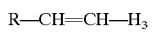

and "deep internal olefins" which are di-substituted olefins in which the double bond is further towards the center of the olefin as in:

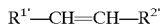

wherein $R^{1'}$ and $R^{2'}$ are different by two or four carbon numbers and are aliphatic hydrocarbon groups containing two or more carbon atoms.

The "beta-internal olefins" referred to herein are monomeric. This means they contain the same number of carbon atoms as the initial vinyl-olefins but the olefinic double bond has moved toward the center of the molecule, by just one carbon number (i.e., the double bond is at the second carbon number).

The "deep internal olefins" referred to herein are dimers of the initial vinyl olefins. For example, a deep internal dimer of 1-octene contains 16 carbon atoms. They differ from vinylidene dimers in that their olefinic double bond is in the linear chain near the center of the molecule.

The olefins used in making the vinylidene olefin are predominately (at least 50 mole percent) $C_4$ to $C_{20}$ straight- or branched-chain monoolefinically unsaturated hydrocarbons (but not less than 5 mole percent) in which the olefinic unsaturation occurs at the 1- or alpha-position of the carbon chain. Typically they have the following formula

$$R^2-(CH_2)_m-CH=CH_2 \quad \text{Formula I}$$

where $R^2$ is hydrogen or alkyl, i.e, $C_1$ to $C_{16}$ linear or branched alkyl, preferably $C_1$ to $C_6$ linear or branched alkyl, most preferably $C_1$ to $C_4$ linear or branched alkyl, e.g. methyl, ethyl and the like, and m is an integer from 0 to 18.

Linear alpha-olefins are commercially available and can be made by the thermal cracking of paraffinic hydrocarbons or by the well-known Ziegler ethylene chain growth and displacement on trialkyl aluminum. Individual olefins may be used as well as mixtures of such olefins. Examples of such olefins are 1-hexene, 1-heptene, 1-octene, 1-nonene, 1-decene, 1-dodecene, 1-hexadecene and 1-tetra-decene. The more preferred normal alpha-olefin monomers are those containing about 8–18 carbon atoms.

The olefin monomers can also contain minor amounts of from 5 up to about 50 and usually less than 25 mole percent of internal olefins and vinylidene olefins. Typically above 70% of said olefin monomers is 8–18 carbon number.

The alpha-olefin of Formula I is contacted with a catalytically effective amount of a catalyst mixture comprising an alkyl aluminum alkoxide.

The alkyl aluminum alkoxide catalyst has the formula $R^4_n Al(OR^5)_p$ where $R^4$ and $R^5$ are alkyl as defined above, n is from 0.75 to 2.75, p is from 0.25 to 2.25 and sum of n and p is 3. Thus, the alkyl aluminum alkoxide $R^4_{1.5} Al(OR^5)_{1.5}$ can be a 1:1 mixture of $R^4 Al(OR^5)_2$ and $(R^4)_2 AlOR^5$. The compound $R^4 Al(OR^5)_2$ can be a minor amount in the mixture with $(R^4)_2 AlOR^5$, e.g., it can be about 5% in $R^4_{1.95} Al(OR^5)_{1.05}$. Preferably, p is about 0.5 to 1.8.

The alkyl aluminum alkoxide is readily formed by processes well known to those skilled in the art, i.e., by reaction of a trialkylaluminum with an aliphatic alcohol, e.g., a $C_1$ to $C_{20}$ linear or branched aliphatic alcohol such as n-butyl alcohol, n-hexyl alcohol, n-octyl alcohol, etc. Alcohol mixtures may also be used. Alternatively, oxidation of trialkyl aluminum may be carried out by air or oxygen under controlled conditions.

The catalytic mixture, present with the vinyl olefin at the time of dimerization is from about 0.02 to about 0.3 of feed molar ratio of aluminum to vinyl. Catalyst concentrations higher than 0.3 feed molar ratio may be used, if desired, but offer no particular advantage over lesser concentrations. For a typical dimerization reaction as contemplated by the present invention, catalyst concentrations within the range of 0.04 to about 0.20 aluminum/vinyl feed molar ratio are preferred.

The dimerization reaction is conducted in a sealed vessel without air at a temperature that is not as low as to retard reaction but not too high such that catalyst activity is diminished due to catalyst decomposition. Thus temperatures in the range of 100° C. to 250° C. have been found conducive to the dimerization reaction, with a range of 120° C. to 200° C. being preferred and 120° C. to 180° C. being most preferred.

The alkyl aluminum alkoxide admixture that is the catalyst of this invention is typically preformed and added to the reaction mixture as such or it may be formed in situ. Thus, for example, a mixture of the alkyl aluminum alkoxide compound, optionally in an inert solvent, may be added to the vinyl olefin to accomplish the present dimerization.

It is also possible to first add the alkyl aluminum alkoxide precursor, i.e., the trialkylaluminum to the olefin reaction mass having the aliphatic alcohol already present. After a period of time suitable to convert the trialkylaluminum into the catalytically active alkyl aluminum alkoxide species (as described herein) the mixture is heated and dimerization effected.

The most preferred embodiment of the invention is a process for dimerizing a mixture of olefins containing about 4–20 carbon atoms consisting mainly of vinyl olefins and a minor amount of vinylidene and internal olefins. The process comprises heating the mixture of olefins in contact with an alkyl aluminum alkoxide of the formula $R^4_n Al(OR^5)_p$, where n+p=3.

EXAMPLES

First, 2499 g or 17.8 g mole of 1-decene (MW=140) is charged into a 3 liter glassware reactor. Next, 218 g or 0.594 g mole of TNOA (Tri Normal Octyl Aluminum, MW=367) is then charged in to the reactor to be mixed with 1-decene. The feed molar ratio of aluminum to vinyl is 0.033 (0.594/17.8=0.033). Then 38.5 g or 0.296 g mole of n-octanol (MW=130) is added to the 1-decene/TNOA mixture slowly while the reaction mixture is stirred. There is a heat release due to oxidation of TNOA. The extent of oxidation of TNOA is 17%. (Note that there are three octyl groups attached to an aluminum molecule, so the extent of oxidation is 0.296/(0.594×3)=17%.)

The reaction mixture is then brought up to the reaction temperature, in this particular example, 170° C. The reaction mixtures during the reaction period are sampled, acid washed, and analyzed by GC and NMR.

Table 1 is the composition (Mol % by NMR) of the reaction mixtures at various times. This represents selectivity of 9 wt %, 9 wt % and 82 wt % for beta internal monomer, deep internal dimer and vinylidene dimer, respectively. This compares favorably with example 6 in the U.S. Pat. No. 4,973,788 with selectivity of 15 wt %, 14 wt % and 71 wt % for these three components, respetively. Example 6 in U.S. Pat. No. 4,973,788 was run with aluminum/vinyl feed molar ratio 0.043, at 170° C. and without oxidation.

TABLE 1

Reaction path at 170° C., aluminum / vinyl feed molar ratio 0.33, 17% oxidized by n-octanol

| Time | Mol% | | | |
|---|---|---|---|---|
| Hr | Vinyl | Beta Internal | Deep Internal | Vinylidene |
| 0 | 91.97 | 2.02 | 0.30 | 5.72 |
| 0.17 | 82.3 | 3.95 | 0.91 | 12.8 |
| 0.42 | 67.9 | 5.14 | 3.5 | 23.5 |
| 1.42 | 50.2 | 8.84 | 4.57 | 36.4 |
| 1.92 | 35.6 | 12.0 | 5.34 | 47.2 |
| 2.42 | 33.3 | 11.4 | 6.16 | 49.1 |
| 3.42 | 27.5 | 12.5 | 6.46 | 53.5 |
| 3.92 | 22.6 | 13.5 | 6.41 | 57.5 |
| 4.42 | 20.83 | 13.74 | 7.74 | 57.69 |
| 4.92 | 16.99 | 13.58 | 7.79 | 61.62 |
| 5.42 | 16.42 | 15.87 | 5.66 | 62.05 |
| 5.92 | 12.85 | 15.28 | 6.8 | 65.07 |

General Procedure

Mixture of TNOA, 1-decene and 1-dodecene is prepared with feed molar ratio of 1/3:1:1 (aluminum/vinyl feed molar ratio=0.17). Stoichiometric amount of 1-hexanol is added to the mixture for corresponding percent oxidation of aluminum alkyl. The reaction between aluminum alkyl and alcohol to form aluminum alkoxide and paraffin is quantitative. The experiments cover 0%, 11% and 20% oxidation. Reactor temperatures are 120°, 140° and 160° C. The reactor is glassware with nitrogen blanket.

Progress of reaction is analyzed by both GC and NMR. Analytical from GC and NMR are consistent. Mol percent from NMR data are provided. Vinyl is starting alpha olefin monomer. Beta Internal is monomer isomer. Vinylidene and deep internal olefins are dimers. In terms of wt %, vinylidene and deep internal dimer olefins are much greater than those shown by mole %, because vinyl and beta internal olefins are monomers.

Example 1

| | Mole % | | | |
|---|---|---|---|---|
| Time/Hr. | Vinyl | Beta Internal | Deep Internal | Vinylidene |
| A1: Temperature: 120° C.; Oxidation: 0% | | | | |
| 0 | 93.3 | 2.0 | 0.5 | 4.2 |
| 0.167 | 93.2 | 1.5 | 1.0 | 4.3 |
| 0.333 | 92.6 | 1.9 | 1.0 | 4.5 |
| 0.5 | 92.2 | 1.6 | 1.2 | 4.9 |
| 0.667 | 91.6 | 2.2 | 1.0 | 5.2 |
| 0.833 | 91.2 | 2.5 | 1.0 | 5.3 |
| 1.0 | 90.3 | 2.5 | 1.2 | 6.0 |
| 1.5 | 88.8 | 3.1 | 1.0 | 7.1 |
| 2.0 | 86.6 | 4.2 | 0.9 | 8.3 |
| 2.5 | 83.8 | 4.6 | 1.8 | 9.8 |
| 3.0 | 81.8 | 5.7 | 1.5 | 11.0 |
| A2: Temperature: 120° C.; Oxidation: 11% | | | | |
| 0 | 93.2 | 2.2 | — | 4.6 |
| 0.167 | 92.8 | 2.2 | 0.4 | 4.6 |
| 0.333 | 92.6 | 2.5 | 0.1 | 4.8 |
| 0.5 | 92.4 | 2.6 | 0.1 | 4.9 |
| 0.667 | 91.7 | 2.9 | 0.3 | 5.1 |
| 0.833 | 91.7 | 2.7 | 0.3 | 5.3 |
| 1.0 | — | — | — | — |
| 1.5 | 90.1 | 3.0 | 0.8 | 6.1 |
| 2.0 | 88.7 | 4.0 | 0.2 | 7.1 |
| 2.5 | 87.0 | 4.5 | 0.2 | 8.3 |
| 3.0 | 85.9 | 3.7 | 1.1 | 9.2 |

Example 2

| | Mole % | | | |
|---|---|---|---|---|
| Time/Hr. | Vinyl | Beta Internal | Deep Internal | Vinylidene |
| B1: Temperature: 140° C.; Oxidation: 0% | | | | |
| 0 | 92.7 | 1.1 | 1.0 | 4.7 |
| 0.167 | 91.4 | 1.5 | 1.7 | 5.4 |
| 0.333 | 88.4 | 2.2 | 1.5 | 7.5 |
| 0.5 | 86.4 | 2.7 | 1.7 | 9.2 |
| 0.667 | 83.1 | 3.5 | 2.3 | 11.1 |
| 0.833 | 79.4 | 4.6 | 3.2 | 12.8 |
| 1.0 | 75.9 | 6.1 | 2.7 | 14.4 |
| 1.5 | 67.1 | 9.0 | 3.8 | 20.1 |
| 2.0 | 59.7 | 11.3 | 4.2 | 24.8 |
| 2.5 | 50.8 | 14.4 | 5.6 | 29.2 |
| 3.0 | 42.4 | 17.4 | 6.9 | 33.3 |
| B2: Temperature: 140° C.; Oxidation: 11% | | | | |
| 0 | 92.4 | 2.3 | 0.2 | 5.2 |
| 0.167 | 90.4 | 3.0 | 0.4 | 6.2 |
| 0.333 | 89.4 | 3.3 | 1.3 | 6.0 |
| 0.5 | 87.4 | 4.3 | 0.6 | 7.7 |
| 0.667 | 86.2 | 4.4 | 0.7 | 8.6 |
| 0.833 | 84.6 | 5.7 | 0.9 | 8.7 |
| 1.0 | 81.5 | 6.2 | 1.4 | 10.9 |
| 1.5 | 76.8 | 7.7 | 1.9 | 13.7 |
| 2.0 | 71.7 | 9.3 | 1.9 | 17.1 |
| 2.5 | 67.6 | 12.3 | 0.9 | 19.3 |
| 3.0 | 61.0 | 13.6 | 2.3 | 23.1 |

Example 3

| | Mole % | | | |
|---|---|---|---|---|
| Time/Hr. | Vinyl | Beta Internal | Deep Internal | Vinylidene |
| C1: Temperature: 160° C.; Oxidation: 0% | | | | |
| 0 | 91.6 | 1.9 | 1.0 | 5.5 |
| 0.167 | 85.6 | 3.1 | 1.6 | 9.7 |
| 0.333 | 77.7 | 5.2 | 2.3 | 14.8 |
| 0.5 | 69.8 | 6.5 | 3.6 | 20.1 |
| 0.667 | 63.1 | 8.2 | 4.1 | 24.6 |
| 0.833 | 56.1 | 10.3 | 4.8 | 28.8 |
| 1.0 | 51.1 | 13.0 | 4.6 | 31.3 |
| 1.5 | 37.1 | 15.1 | 7.8 | 40.0 |
| 2.0 | 25.9 | 19.8 | 8.1 | 46.3 |
| 2.5 | 18.7 | 21.8 | 9.8 | 49.8 |
| 3.0 | 14.3 | 23.0 | 11.7 | 51.0 |
| C2: Temperature: 160° C.; Oxidation: 11% | | | | |
| 0 | 88.1 | 4.3 | 0.9 | 6.8 |
| 0.167 | 83.7 | 5.3 | 1.5 | 9.5 |
| 0.333 | 78.7 | 8.1 | 2.7 | 11.6 |
| 0.5 | 71.5 | 9.9 | 2.7 | 15.9 |
| 0.667 | 65.7 | 13.8 | 2.9 | 17.5 |
| 0.833 | 59.5 | 14.1 | 3.9 | 22.4 |
| 1.0 | 52.8 | 16.8 | 3.9 | 22.4 |
| 1.5 | 43.5 | 20.4 | 5.6 | 30.5 |
| 2.0 | 33.2 | 23.9 | 7.8 | 35.1 |
| 2.5 | 28.6 | 27.0 | 8.3 | 36.1 |
| 3.0 | 18.9 | 33.0 | 9.9 | 38.2 |
| C3: Temperature: 160° C.; Oxidation: 20% | | | | |
| 0 | 89.2 | 3.7 | 1.9 | 5.2 |
| 0.167 | 86.1 | 6.2 | 1.6 | 6.1 |
| 0.333 | 80.1 | 10.3 | 0.8 | 8.8 |
| 0.5 | 75.7 | 13.8 | 0.9 | 9.5 |
| 0.667 | 71.0 | 15.7 | 1.5 | 11.8 |
| 0.833 | 66.3 | 17.8 | 2.6 | 13.4 |
| 1.0 | 62.6 | 19.1 | 3.3 | 15.0 |
| 1.5 | 52.5 | 24.9 | 4.5 | 18.1 |
| 2.0 | 43.3 | 29.2 | 5.8 | 21.7 |
| 2.5 | 34.1 | 34.5 | 6.5 | 24.9 |
| 3.2 | 26.2 | 37.5 | 8.4 | 27.9 |

What is claimed is:

1. A process for producing a vinylidene olefin of the formula

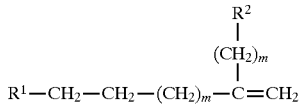

where $R^1$ and $R^2$ are the same or different and are hydrogen or alkyl and m is an integer of from 0 to 18, comprising heating a vinyl olefin of the formula $R^2$—$(CH_2)_m$—CH=$CH_2$ in the presence of a catalyst consisting essentially of an aluminum alkoxide compound of the formula $R^4{}_n$Al$(OR^5)_p$ where $R^4$ and $R^5$ are the same or different and are alkyl, n is from 0.75 to 2.75, and p is from 0.25 to 2.25, the sum of n and p being 3, at an aluminum vinyl feed molar ratio of 0.02 and above and at a temperature of from about 100° C. to about 250° C., whereby the aforesaid vinyl olefin is dimerized to produce the aforesaid vinylidene olefin and a deep internal olefin dimer.

2. The process of claim 1 wherein $R^1$ and R2 are hydrogen.

3. The process of claim 1 wherein $R^2$ is a $C_2$–$C_{16}$ branched aliphatic hydrocarbon group.

4. The process of claim 1 wherein said temperature is about 120° C. to 200° C.

5. A process wherein a mixture of alpha olefins containing about 4–20 straight or branched chain carbon atoms, said mixture of olefins consisting essentially of 50 to 95 weight percent of vinyl olefins and 5 to 50 weight percent of vinylidene olefins and internal olefins is dimerized by heating said mixture of olefins in contact with a catalyst consisting essentially of an alkyl aluminum alkoxide compound at an aluminum/vinyl feed molar ratio of 0.02 to 0.3 and at a temperature of about 120° C. to 180° C. until said vinyl olefins have dimerized to form a vinylidene olefin having the formula shown in claim 1.

6. The process of claim 5 wherein at least 70 weight percent of the alpha olefins in said mixture of olefins is octene, decene, dodecene, tetradecene, hexadecene or octadecene.

\* \* \* \* \*

UNITED STATES PATENT AND TRADEMARK OFFICE
CERTIFICATE OF CORRECTION

PATENT NO.: 5,824,833
DATED: October 20, 1998
INVENTOR(S): Kaung-Far Lin

It is certified that error appears in the above-identified patent and that said Letters Patent is hereby corrected as shown below:

Patent reads:

| Col. | Line | |
|---|---|---|
| 2 | 43 | "R—CH=CH—H$_3$"<br>should read -- R—CH=CH—CH$_3$ -- |
| 3 | 19 | "monomers can also contain minor amounts of from"<br>should read --monomers can also contain from-- |
| 4 | 15 | "is then charged"<br>should read --is charged-- |
| 6 | 60 | "wherein R$^1$ and R2 are"<br>should read --wherein R$^1$ and R$^2$ are-- |

Signed and Sealed this

Ninth Day of February, 1999

Attest:

Attesting Officer

Acting Commissioner of Patents and Trademarks